United States Patent
Yoshiara et al.

(10) Patent No.: US 9,201,139 B2
(45) Date of Patent: Dec. 1, 2015

(54) ULTRASONIC DIAGNOSTIC APPARATUS, ULTRASONIC IMAGE PROCESSING APPARATUS, AND MEDICAL IMAGE DIAGNOSTIC APPARATUS

(75) Inventors: Hiroki Yoshiara, Nasushiobara (JP); Naohisa Kamiyama, Otawara (JP); Tetsuya Yoshida, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 378 days.

(21) Appl. No.: 13/152,675

(22) Filed: Jun. 3, 2011

(65) Prior Publication Data
US 2011/0301457 A1 Dec. 8, 2011

(30) Foreign Application Priority Data
Jun. 8, 2010 (JP) .................................. 2010-131421

(51) Int. Cl.
A61B 8/08 (2006.01)
G01S 7/52 (2006.01)
A61B 6/00 (2006.01)

(52) U.S. Cl.
CPC .............. *G01S 7/52071* (2013.01); *A61B 8/08* (2013.01); *G01S 7/52026* (2013.01); *G01S 7/52074* (2013.01); *A61B 6/481* (2013.01); *A61B 6/504* (2013.01)

(58) Field of Classification Search
USPC .......................................... 600/407, 437–472
See application file for complete search history.

(56) References Cited

U.S. PATENT DOCUMENTS

| 2005/0059893 A1* | 3/2005 | Ogasawara et al. ........... 600/454 |
| 2007/0073146 A1 | 3/2007 | Phillips et al. |
| 2008/0294049 A1* | 11/2008 | Guracar ......................... 600/458 |
| 2009/0253986 A1 | 10/2009 | Frinking et al. |

(Continued)

FOREIGN PATENT DOCUMENTS

| CN | 1943516 A | 4/2007 |
| CN | 101170947 A | 4/2008 |

(Continued)

OTHER PUBLICATIONS

Extended European Search Report issued Nov. 3, 2011, in European Patent Application No. 11168963.4.

(Continued)

*Primary Examiner* — Mark Remaly
(74) *Attorney, Agent, or Firm* — Oblon, McClelland, Maier & Neustadt, L.L.P.

(57) ABSTRACT

According to one embodiment, an ultrasonic diagnostic apparatus which comprises an ultrasonic transmission/reception unit configured to transmit ultrasonic waves to a scan area including a predetermined region throughout an analysis period, receive reflected waves from the scan area, and acquire ultrasonic data associated with the scan area for each phase in the analysis period, an analysis unit configured to generate a luminance time curve associated with at least one analysis area included in the scan area by using the ultrasonic data in each phase in the analysis period and analyze a stagnant time of the contrast medium associated with at least one analysis area based on the generated luminance time curve, an image generation unit configured to generate a stagnant time image for each phase in the analysis period, with different hues being assigned to at least one analysis area in accordance with the stagnant times.

24 Claims, 8 Drawing Sheets

(56) References Cited

U.S. PATENT DOCUMENTS

| | | |
|---|---|---|
| 2009/0299182 A1 | 12/2009 | Asafusa |
| 2010/0094133 A1 | 4/2010 | Yoshiara et al. |
| 2011/0015522 A1 | 1/2011 | Arditi et al. |

FOREIGN PATENT DOCUMENTS

| | | |
|---|---|---|
| CN | 101305399 A | 11/2008 |
| EP | 1 767 961 A1 | 3/2007 |
| EP | 1 884 195 A1 | 2/2008 |
| JP | 7-79981 | 3/1995 |
| JP | 11-137552 A | 5/1999 |
| JP | 2001-269341 | 10/2001 |
| JP | 2004-321688 | 11/2004 |
| JP | 2009-82181 | 4/2009 |
| JP | 2010-94220 | 4/2010 |
| WO | WO 2007/054544 A1 | 5/2007 |
| WO | WO 2009/037484 A2 | 3/2009 |
| WO | WO 2009/037484 A3 | 3/2009 |
| WO | WO 2009/083557 A1 | 7/2009 |
| WO | WO 2009/110308 A1 | 9/2009 |

OTHER PUBLICATIONS

M. Hughes, et al., "Ultrasonic Molecular Imaging of Primordial Angiogenic Vessels in Rabbit and Mouse Models with $\alpha_v\beta_3$-integrin Targeted Nanoparticles Using Information-Theoretic Signal Detection: Results at High Frequency and in the Clinical Diagnostic Frequency Range", 2005 IEEE Ultrasonics Symposium, vol. 1, XP-010898816, Sep. 18, 2005, pp. 617-620.

A. Stoian, et al., "Information System for Tumor Angiogenesis Phenomena Imaging Monitor", Automation, Quality and Testing, Robotics, 2006 IEEE International Conference on IEEE., XP-031024081, May 1, 2006, 5 pages.

Ara Kassarjian, MD, et al., "Angiographic Classification of Hepatic Hemangiomas in Infants" Radiology, vol. 222, No. 3, XP-002661729, Mar. 2002, pp. 693-698.

Rakesh K. Jain, "Normalization of Tumor Vasculature: An Emerging Concept in Antiangiogenic Therapy", Science, vol. 307, Jan. 7, 2005, pp. 58-62.

Madoka Yamazaki, et al., "Sonic hedgehog derived from human pancreatic cancer cells Augments angiogenic function of endothelial progenitor cells", Cancer Sci. vol. 99, No. 6, Jun. 2008, pp. 1131-1138.

Combined Notification of the First Office Action and Search Report issued Dec. 13, 2012 in Chinese Patent Application No. 201110151213.0 (with English translation).

Office Action issued May 7, 2014 in Japanese Patent Application No. 2010-131421filed Jun. 8, 2010 (with English Translation).

Office Action dated Dec. 17, 2013, in Japanese Patent Application No. 2010-131421 (with English translation).

A. Needles, et al., "A Method for Differentiating Targeted Microbubbles in Real Time Using Subharmonic Micro-Ultrasound and Interframe Filtering", Ultrasound in Medicine & Biology, vol. 35, No. 9, 2009, pp. 1564-1573.

Ryan Gessner, et al., "Advances in Molecular Imaging with Ultrasound", Molecular Imaging, vol. 9, No. 3, May-Jun. 2010, pp. 117-127.

\* cited by examiner

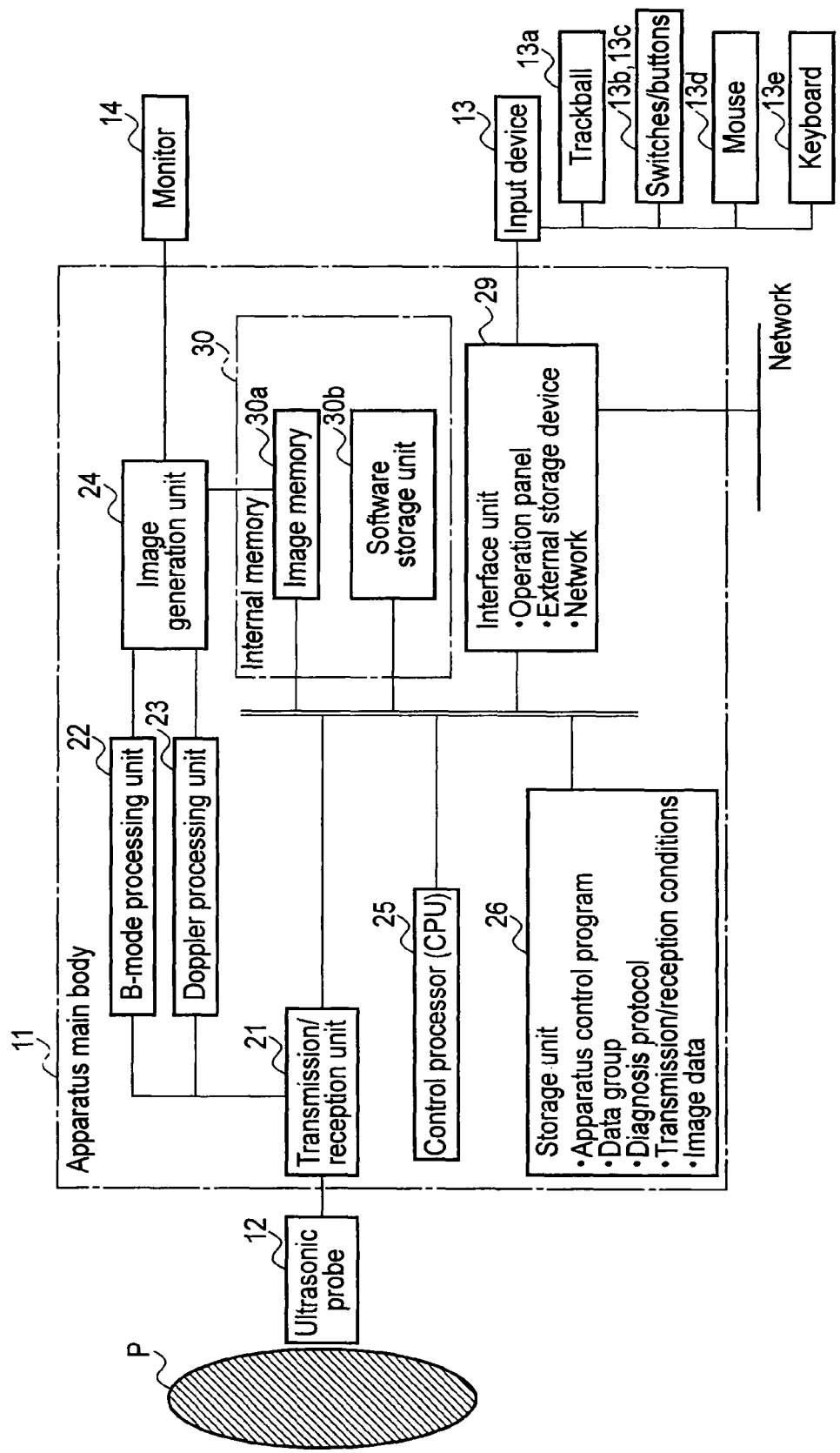
F I G. 1

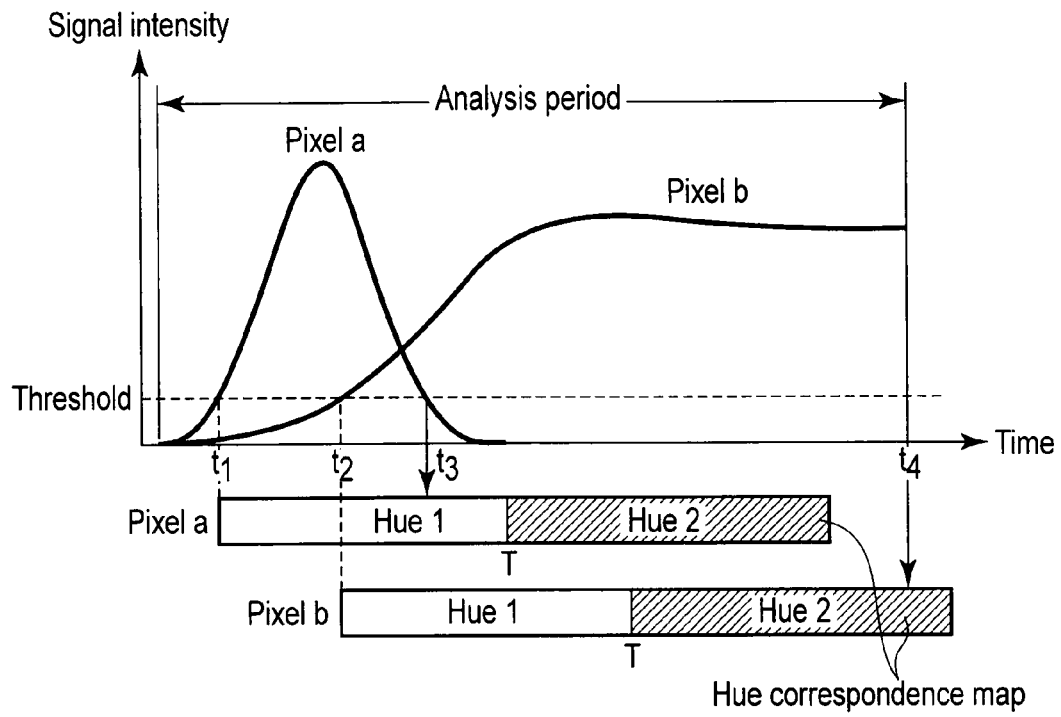
F I G. 5
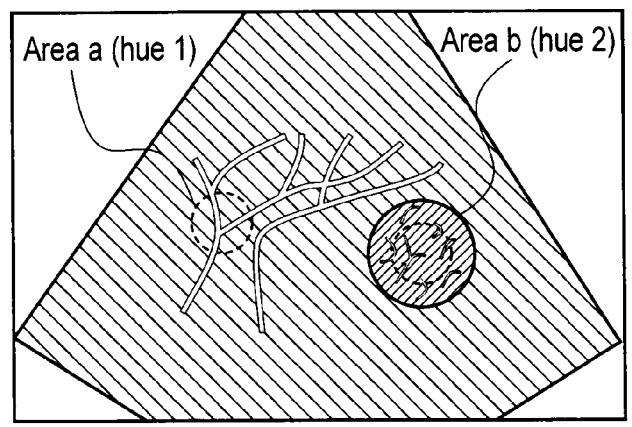
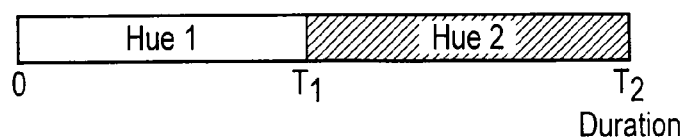
F I G. 6

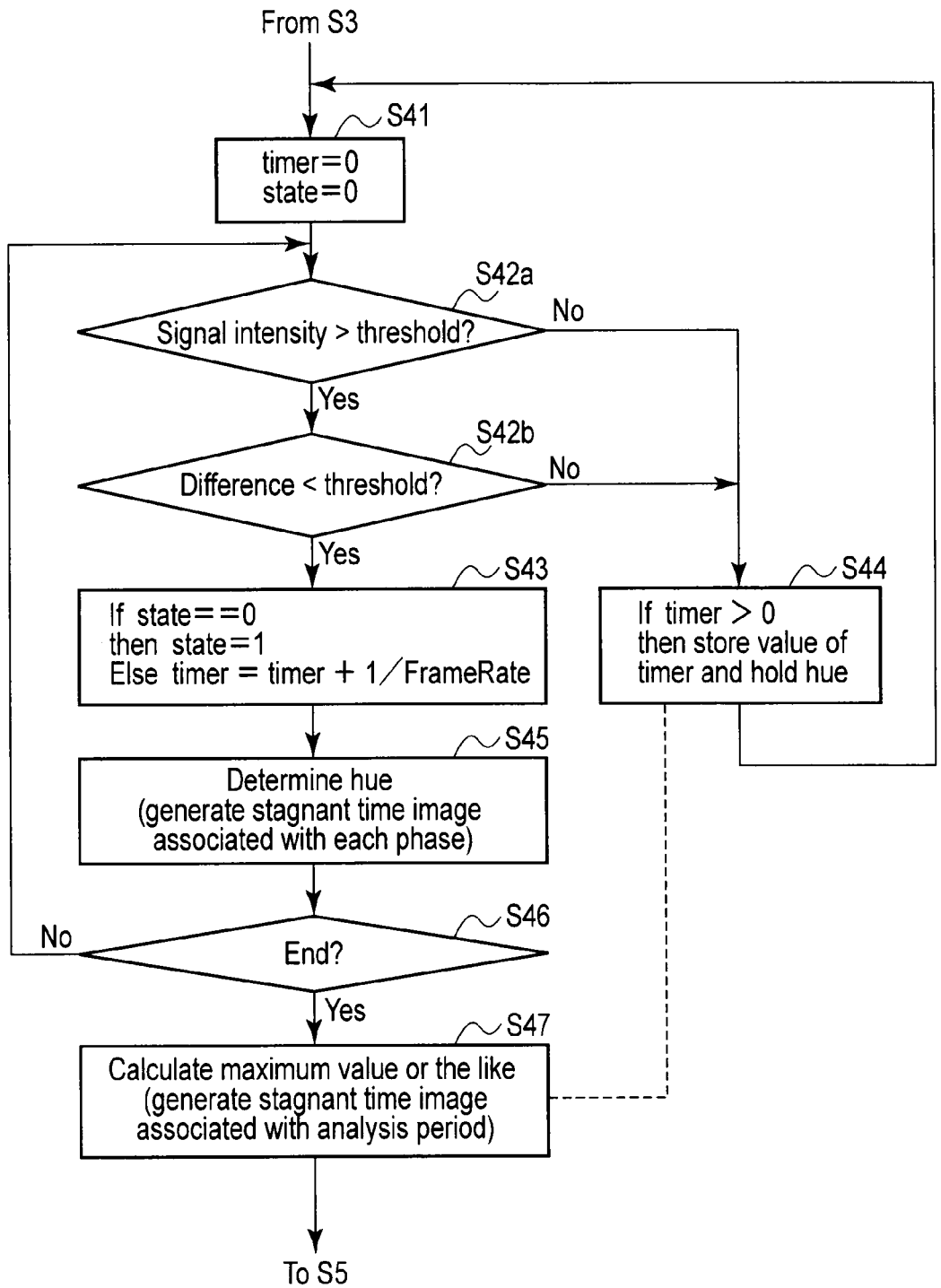
F I G. 12

US 9,201,139 B2

ULTRASONIC DIAGNOSTIC APPARATUS, ULTRASONIC IMAGE PROCESSING APPARATUS, AND MEDICAL IMAGE DIAGNOSTIC APPARATUS

CROSS-REFERENCE TO RELATED APPLICATIONS

This application is based upon and claims the benefit of priority from Japanese Patent Application No. 2010-131421, filed Jun. 8, 2010; the entire contents of which are incorporated herein by reference.

FIELD

Embodiments described herein relate generally to an ultrasonic diagnostic apparatus, an ultrasonic image processing apparatus, and a medical image diagnostic apparatus.

BACKGROUND

Ultrasonic diagnosis allows to display in real time how the heart beats or the fetus moves, by simply bringing an ultrasonic probe into contact with the body surface. This technique is highly safe, and hence allows repetitive examination. Furthermore, this system is smaller in size than other diagnostic apparatuses such as X-ray, CT, and MRI apparatuses and can be moved to the bedside to be easily and conveniently used for examination. In addition, ultrasonic diagnostic apparatuses vary in type depending on the functions which they have. Some compact apparatuses which have already been developed are small enough to be carried with one hand, and ultrasonic diagnosis is free from the influence of radiation exposure unlike diagnosis using X-rays. Therefore, such ultrasonic diagnostic apparatuses can be used in obstetric treatment, treatment at home, and the like.

Recently, intravenous-type ultrasonic contrast media (to be simply referred to as contrast media hereinafter) have been commercialized, and a "contrast echo method" has been practiced. This technique aims at hemodynamics evaluation upon enhancement of a blood flow signal by injecting an ultrasonic contrast medium through a vein in, for example, cardiac and hepatic examinations. Many contrast media function by using microbubbles as reflection sources. For example, a second-generation ultrasonic contrast medium called Sonazoid® which has recently been released in Japan comprises microbubbles each covered with a phospholipid film and containing a perfluorobutane gas. It has become possible to stably observe how a contrast medium refluxes, using ultrasonic transmission waves with an amplitude small enough not to destroy microbubbles.

Scanning a diagnostic region (e.g., liver cancer) after the administration of a contrast medium allows to observe increases and decreases in signal intensity from the inflow of a contrast medium, which circulates on a blood flow, to the outflow of the contrast medium. Studies have been made to enable benignancy/malignancy differential diagnosis of a tumoral lesion or diagnosis of a "diffuse" disease or the like based on such differences in temporal changes in signal intensity.

In general, such temporal changes in signal intensity need to be recorded or interpreted as a moving image unlike simple morphological information. This generally leads to a long time required for interpretation. Under the circumstance, there has been proposed a technique of mapping the inflow time information of a contrast medium to be generally observed in moving images onto a single still image (see Jpn. Pat. Appln. KOKAI Publication No. 2001-269341, and Jpn. Pat. Appln. KOKAI Publication No. 2004-321688). Such a technique expresses, with different hues, the differences between the peak times of signals based on a contrast medium and allows to recognize at a glance the inflow time at each position within a diagnostic slice.

In tumor blood vessels which run in a complicated manner as compared with normal blood vessels, a phenomenon is observed, in which bubbles have nowhere to go and become stagnant or reflux after stagnation (see R. K. Jain, "Normalization of Tumor Vasculature: An Emerging Concept in Anti-angiogenetic Therapy", Science, Vol. 307, pp. 58-62, January 2005). In practice, when performing contrast medium ultrasonic observation using a tumor mouse, the behavior of bubbles like that described above is observed in tumor blood vessels. If it is possible to evaluate the behavior of bubbles with contrast-enhanced ultrasonic waves which enable biological imaging, there is a possibility that this technique can be applied to the evaluation of abnormality of tumor blood vessels.

It has been confirmed by histopathological observation that an antiangiogenic agent (anticancer agent) which has currently been clinically tested fragments/confines tumor blood vessels by destroying blood vessels that nourish the tumor (see M. Yamazaki, et al., "Sonic hedgehog derived from human pancreatic cancer cells augments angiogenic function of endothelial progenitor cells", Cancer Science, Vol. 99(6), pp. 1131-1138). If it is possible to visualize and quantify, with contrast-enhanced ultrasonic waves, the manner of how bubbles become stagnant in blood vessels fragmented by the antiangiogenic agent, this technique can be expected to be applied to treatment effect determination.

However, mapping of contrast medium inflow times (arrival times) using a conventional ultrasonic diagnostic apparatus cannot express characteristics after the arrival of the contrast medium. For example, it is not possible to discriminate between, for example, a state in which a contrast medium is continuously flowing into a given area and new microbubbles (to be simply referred to as bubbles hereinafter) are replacing old bubbles and a state in which bubbles that have flowed into the area are stagnant.

Note that, for example, the technique disclosed in Jpn. Pat. Appln. KOKAI Publication No. 2001-269341 displays contrast medium inflow information (e.g., arrival times) in an ultrasonic scanning slice by color mapping with reference to a given time, and hence allows to observe, in an entire image, how a contrast medium flows into each area. However, this technique does not allow sufficient evaluation of the stagnant state of bubbles after the arrival of the contrast medium at each area. In addition, the technique disclosed in Jpn. Pat. Appln. KOKAI Publication No. 2004-321688 can present the information of arrival times by performing more precise computation based on a logical model of the reflux of microcirculatory blood flows. However, even this technique cannot sufficiently evaluate the stagnant state of bubbles after the arrival of a contrast medium at each area.

BRIEF DESCRIPTION OF THE DRAWINGS

FIG. 1 is a block diagram showing the arrangement of an ultrasonic diagnostic apparatus 10 according to the first embodiment;

FIG. 5 is a graph for explaining the principle of the processing of generating a stagnant time image;

FIG. 6 is a view showing an example of a stagnant time image displayed while being updated in chronological order;

FIG. 12 is a flowchart showing a procedure for the processing of generating a stagnant time image according to the second embodiment.

DETAILED DESCRIPTION

Figure 2:
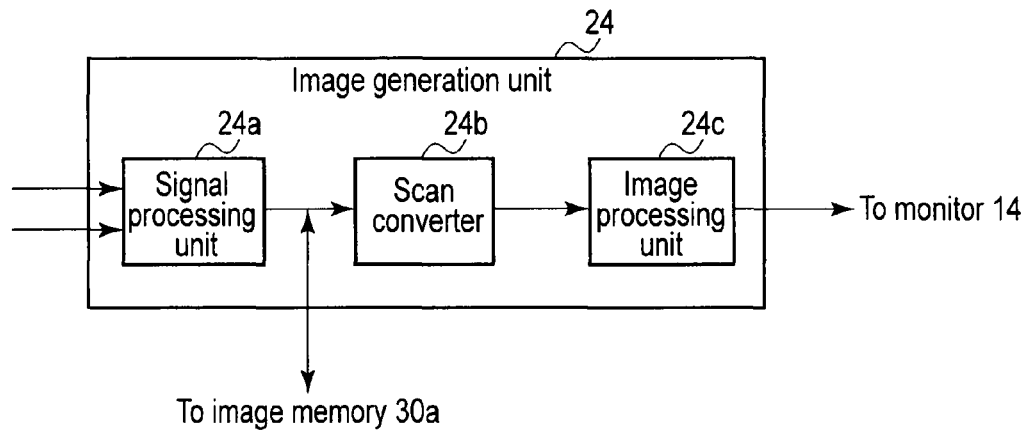
FIG. 2 is a block diagram for explaining the arrangement of an image generation unit 24.

In general, according to one embodiment, an ultrasonic diagnostic apparatus which acquires an ultrasonic image by scanning, with ultrasonic waves, a predetermined region of an object to which a contrast medium is administered includes an ultrasonic transmission/reception unit configured to transmit ultrasonic waves to a two-dimensional area or a three-dimensional area, which includes the predetermined region, as a scan area throughout an analysis period, receive reflected waves from the scan area, and acquire ultrasonic data associated with the scan area for each phase in the analysis period, an analysis unit configured to generate a luminance time curve associated with at least one analysis area included in the scan area by using the ultrasonic data in each phase in the analysis period and analyze a stagnant time of the contrast medium associated with at least one analysis area based on the generated luminance time curve, an image generation unit configured to generate a stagnant time image for each phase in the analysis period, with different hues being assigned to at least one analysis area in accordance with the stagnant times, and a display unit configured to display the stagnant time image for each phase.

The first and second embodiments will be described below with reference to the views of the accompanying drawing. Note that the same reference numerals in the following description denote constituent elements having almost the same functions and arrangements, and a repetitive description will be made only when required. For the sake of a concrete description, the following description will exemplify a case in which the contrast medium stagnant information generation function to be described later is implemented in an ultrasonic diagnostic apparatus. However, the contrast medium stagnant information generation function described in each embodiment can be implemented in other medical image diagnostic apparatuses such as an X-ray computed tomography apparatus, a magnetic resonance imaging apparatus, and an X-ray diagnostic apparatus.

(First Embodiment)

FIG. 1 is a block diagram showing the arrangement of an ultrasonic diagnostic apparatus 10 according to the first embodiment. As shown in FIG. 1, the ultrasonic diagnostic apparatus 10 includes an ultrasonic probe 12, an input device 13, a monitor 14, a transmission/reception unit 21, a B-mode processing unit 22, a Doppler processing unit 23, an image generation unit 24, a control processor 25, a storage unit 26, an interface unit 29, and an internal memory 30. The transmission/reception unit 21 and the like incorporated in an apparatus main body 11 may be implemented by hardware such as an integrated circuit and the like, or may be implemented by software programs as software modules. The function of each constituent element will be described below.

The ultrasonic probe 12 includes a plurality of piezoelectric transducers which generate ultrasonic waves based on driving signals from the transmission/reception unit 21 and convert reflected waves from an object into electrical signals, a matching layer provided for the piezoelectric transducers, and a backing member which prevents ultrasonic waves from propagating backward from the piezoelectric transducers. When the ultrasonic probe 12 transmits ultrasonic waves to an object P, the transmitted ultrasonic waves are sequentially reflected by a discontinuity surface of acoustic impedance of internal body tissue, and are received as an echo signal by the ultrasonic probe 12. The amplitude of this echo signal depends on an acoustic impedance difference on the discontinuity surface by which the echo signal is reflected. The echo produced when a transmitted ultrasonic pulse is reflected by the surface of a moving blood flow, cardiac wall, or the like is subjected to a frequency shift depending on the velocity component of the moving body in the ultrasonic transmission direction due to the Doppler effect.

The input device 13 is connected to the apparatus body 11 and includes a trackball 13a, various types of switches 13b, buttons 13c, a mouse 13d, and a keyboard 13e which are used to input, to the apparatus main body 11, various types of instructions, conditions, an instruction to set a region of interest (ROI), various types of image quality condition setting instructions, and the like from an operator.

The monitor 14 displays morphological information and blood flow information in the living body as images based on video signals from the image generation unit 24.

The transmission/reception unit 21 includes a trigger generation circuit, delay circuit, and pulser circuit (none of which are shown). The pulser circuit repetitively generates rate pulses for the formation of transmission ultrasonic waves at a predetermined rate frequency fr Hz (period: 1/fr sec). The delay circuit gives each rate pulse a delay time necessary to focus an ultrasonic wave into a beam and determine transmission directivity for each channel. The trigger generation circuit applies a driving pulse to the probe 12 at the timing based on this rate pulse.

The transmission/reception unit 21 has a function of instantly changing a transmission frequency, transmission driving voltage, or the like in accordance with an instruction from the control processor 25. In particular, the function of changing a transmission driving voltage is implemented by linear amplifier type transmission circuit capable of instantly switching its value or a mechanism of electrically switching a plurality of power supply units.

The transmission/reception unit 21 includes an amplifier circuit, A/D converter, and adder (none of which are shown). The amplifier circuit amplifies an echo signal received via the probe 12 for each channel. The A/D converter gives the amplified echo signals delay times necessary to determine reception directivities. The adder then performs addition processing for the signals. With this addition, a reflection component from a direction corresponding to the reception directivity of the echo signal is enhanced to form a composite beam for ultrasonic transmission/reception in accordance with reception directivity and transmission directivity.

The B-mode processing unit 22 receives an echo signal from the transmission/reception unit 21, and performs logarithmic amplification, envelope detection processing, and the like for the signal to generate data whose signal intensity is expressed by a luminance level. After the image generation unit 24 performs predetermined processing for this data, the monitor 14 displays the resultant data as a B-mode image whose reflected wave intensity is expressed by a luminance.

The Doppler processing unit 23 frequency-analyzes velocity information from the echo signal received from the transmission/reception unit 21 to extract a blood flow, tissue, and contrast medium echo component by the Doppler effect, and obtains blood flow information such as an average velocity, variance, and power at multiple points. The obtained blood flow information is sent to the image generation circuit 24, and is displayed in color as an average velocity image, a variance image, a power image, and a combined image of them on the monitor 14.

The image generation unit 24 generates an ultrasonic diagnostic image as a display image by converting the scanning line signal string for ultrasonic scanning into a scanning line signal string in a general video format typified by a TV format. The image generation unit 24 incorporates a storage memory which stores image data. The operator can read out images recorded during examination after, for example, diagnosis. Note that data before it is input to the image generation unit 24 is sometimes called "raw data".

FIG. 2 is a block diagram for explaining the arrangement of the image generation unit 24. As shown in FIG. 2, the image generation unit 24 includes a signal processing unit 24a, a scan converter 24b, and an image processing unit 24c. The signal processing unit 24a performs filtering for determining image quality at the scanning line level in ultrasonic scanning. The data processed by the signal processing unit 24a is sent to the scan converter 24b and is simultaneously output to an image memory 30a in the internal memory 30 to be temporarily stored.

The scan converter 24b converts the scanning line signal string for ultrasonic scanning into a scanning line signal string in a general video format typified by a TV format. The data after the conversion is output to the image processing unit 24c. The image processing unit 24c executes image processing such as adjustment of a luminance and contrast and spatial filtering, and the processing of combining the generated image with character information of various types of set parameters, scale marks, and the like, and outputs the resultant data as a video signal to the monitor 14. The image processing unit 24c further executes processing and the like based on the contrast medium stagnant information generation function (to be described later) to generate ultrasonic images, stagnant time images, and the like in accordance with control signals from the control processor 25.

The control processor (CPU) 25 is a control unit which has the function of an information processing apparatus (computer) and controls the operation of the main body of this ultrasonic diagnostic apparatus. The control processor 25 reads out a control program for executing the contrast medium stagnant information generation function (to be described later) from the storage unit 26, expands the program in a software storage unit 30b, and executes computation, control, and the like associated with each type of processing. The control processor 25 further executes quantitative analysis of stagnant times by using generated stagnant time images in the processing based on the contrast medium stagnant information generation function (to be described later).

The storage unit 26 stores control programs for implementing the contrast medium stagnant information generation function (to be described later), various types of scan sequences, image generation, and display processing, hue correspondence maps which defines the correspondence relationship between durations and hues, diagnosis information (patient ID, findings by doctors, and the like), a diagnosis protocol, transmission/reception conditions, and other data. The storage unit 26 is also used to store images in the image memory 30a, as needed. It is possible to transfer data in the storage unit 26 to an external peripheral device via the interface unit 29.

The interface unit 29 is an interface associated with the input device 13, a network, and a new external storage device (not shown). The interface unit 29 can transfer data such as ultrasonic images, analysis results, and the like obtained by this apparatus to another apparatus via a network.

The internal memory 30 includes the image memory 30a and the software storage unit 30b. The image memory 30a temporarily stores the image data received from the signal processing unit 24a for each frame or volume. For example, the operator can read out data stored in the image memory 30a after diagnosis, and can reproduce the data as a still image or a moving image by using a plurality of frames. The image memory 30a also stores an output signal (radio frequency (RF) signal) immediately after it is output from the transmission/reception unit 21, an image luminance signal immediately after it is transmitted through the transmission/reception unit 21, other raw data, image data acquired via the network, and the like, as needed. The software storage unit 30b temporarily stores the dedicated program read out from the storage unit 26 when executing the contrast medium stagnant information generation function (to be described later).

(Contrast Medium Stagnant Information Generation Function)

The contrast medium stagnant information generation function will be described next. This function measures a temporal change in each pixel value in an analysis area set in a scan area (a two-dimensional or three-dimensional area in an object subjected to ultrasonic scanning), analyzes the stagnant time of a contrast medium in the analysis area for each pixel by using the measured temporal change in pixel value, and generates and displays a stagnant time image or the like for the evaluation of the stagnant time of the contrast medium based on the analysis result.

Note that an analysis area set in a scan area is, for example, a two-dimensional or three-dimensional area including a diagnosis target area as an analysis target for the contrast medium stagnant information generation function, and is set by the operator at a predetermined timing. One or a plurality of analysis areas may be set in a scan area. In addition, the entire scan area can be one analysis area. Furthermore, it is possible to arbitrarily set or change the size of each analysis area from the size of an area constituted by a single pixel to the size of an area constituted by a plurality of pixels.

Figure 3:
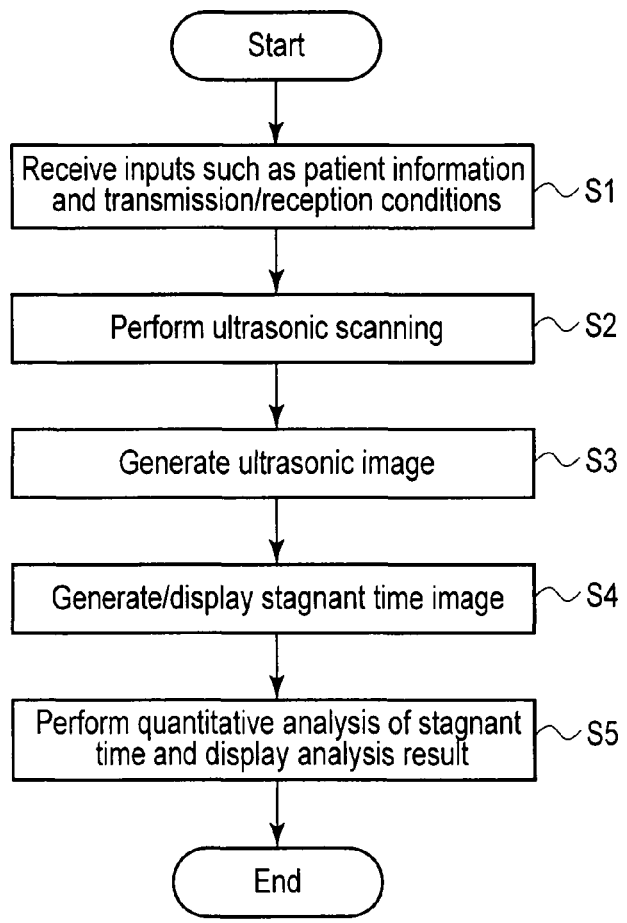
FIG. 3 is a flowchart for explaining a procedure for processing (contrast medium stagnant information generation processing) based on a contrast medium stagnant information generation function according to this embodiment.

FIG. 3 is a flowchart for explaining a procedure for processing (contrast medium stagnant information generation processing) based on this contrast medium stagnant information generation function. The contents of processing to be executed in each step will be described below.

[Reception of Inputs such as Patient Information and Transmission/Reception Conditions: Step S1]

The operator inputs patient information and selects transmission/reception conditions (a field angle, focal position, transmission voltage, and the like for determining the size of a scan area), a scan sequence for ultrasonically scanning a three-dimensional area in an object throughout a predetermined period of time via the input device 13 (step S1). The internal memory 30 or the like automatically stores the input and selected various types of information and conditions and the like.

[Ultrasonic Scanning: Step S2]

The transmission/reception unit 21 then ultrasonically scans an area including a predetermined region (e.g., a blood vessel as a diagnosis target) of an object as a scan area throughout an analysis period as an analysis target, and acquires ultrasonic data (ultrasonic data for each frame) corresponding to each phase in the predetermined period (step S2). For a concrete description, this embodiment will exemplify a case in which two-dimensional scanning is executed for a two-dimensional area as a scan area. However, this embodiment is not limited to this case, and may execute three-dimensional scanning (volume scanning) for a three-dimensional area as a scan area.

[Generation of Ultrasonic Image: Step S3]

The acquired ultrasonic data are sequentially sent to the B-mode processing unit 22 via the transmission/reception unit 21. The B-mode processing unit 22 performs logarithmic amplification, envelope detection processing, and the like for the data to generate image data whose signal intensity is expressed by a luminance. The image generation unit 24 performs harmonic component extraction processing and the like for the generated image data to generate an ultrasonic image (an ultrasonic image for each frame) corresponding to each phase k (k=1, 2, . . . , n) (step S3). The generated ultrasonic image represents the spatial density (density) of the contrast medium at each phase by using a signal value (luminance value).

[Generation of Stagnant Time Image: Step S4]

The image generation unit 24 sequentially generates the TICs (Time Intensity Curves) of the respective pixels in the analysis area by using the ultrasonic images corresponding to the respective phases, and generates a stagnant time image by analyzing the stagnant time of the contrast medium for each pixel in the analysis area by using the generated respective TICs (step S4).

Figure 4:
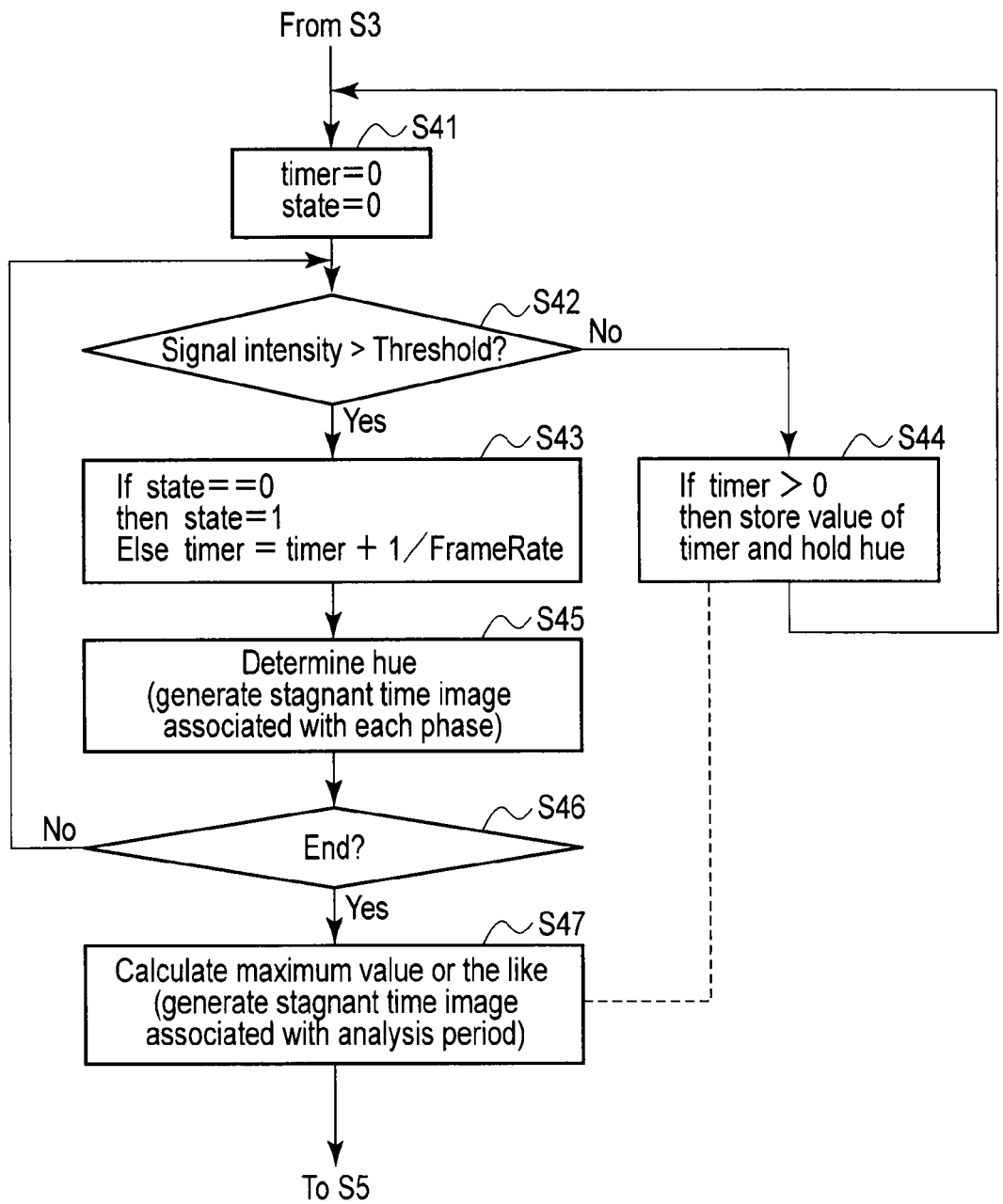
FIG. 4 is a flowchart showing a procedure for the processing of generating a stagnant time image according to the first embodiment.

FIG. 4 is a flowchart showing a procedure for the processing of generating a stagnant time image. The processing of generating a stagnant time image based on this flowchart is executed concurrently for each pixel in an analysis area. FIG. 5 is a graph for explaining the concept of the processing of generating a stagnant time image, and shows TICs and hue correspondence maps respectively associated with a given pixel a in an analysis area a and a given pixel b in an analysis area b.

As shown in FIG. 4, first of all, the image generation unit 24 initializes (resets) a timer to 0 in accordance with a predetermined phase (e.g., the ith phase, where i=1, 2, 3, . . . , n), and starts measuring the duration. The image generation unit 24 also sets a flag representing the presence/absence of a contrast medium to 0 (corresponding to the signal 0 from the contrast medium: "absence of contrast medium") (step S41). Such initialization can exclude a portion having a high signal intensity such as a tissue signal before the inflow of a contrast medium.

The image generation unit 24 then compares the signal intensity with a preset threshold, for the pixel, to determine whether the pixel value exceeds the threshold (i.e., whether a contrast medium exists at a position corresponding to the pixel) (step S42). If the pixel value exceeds the threshold, the image generation unit 24 starts measuring the duration upon setting the flag representing the presence/absence of a contrast medium to 1 (corresponding to "presence of contrast medium"), and keeps measuring the duration by using the timer (step S43). According to the case in FIG. 5, the image generation unit 24 determines, for the pixel a, that the contrast medium arrival time corresponds to time t1 when the pixel value becomes equal to or more than the threshold. The image generation unit 24 then changes the flag representing the presence/absence of a contrast medium from 0 to 1, and continues to measure the duration by using the timer. The image generation unit 24 determines, for the pixel b, that the contrast medium arrival time corresponds to time t2 when the pixel value becomes equal to or more than the threshold. The image generation unit 24 then changes the flag representing the presence/absence of a contrast medium from 0 to 1, and continues to measure the duration by using the timer.

The image generation unit 24 then determines the hue of the pixel at the ith phase (frame) based on the value of the duration timer and the preset hue correspondence map (in the case of FIG. 5, hue 1 is made to correspond to duration≤T, and hue 2 is made to correspond to duration>T) (step S44). Such hue determination processing is executed concurrently for each pixel in an analysis area. As a result, a stagnant time image associated with the ith phase is generated, with the contrast medium stagnant time at each position in the analysis area being represented by a hue, and a signal intensity from the contrast medium at each position in the analysis area being represented by a luminance (step S45). The monitor 14 displays the generated stagnant time image associated with the ith phase, together with the hue correspondence map, in, for example, the form shown in FIG. 6.

The control processor 25 then determines whether to terminate the stagnant time image generation (step S46). If the control processor 25 determines not to terminate the stagnant time image generation, the process returns to step S42. The image generation unit 24 then compares the pixel value of the pixel at the (i+1)th phase with the preset threshold to determine whether the pixel value exceeds the threshold (step S42). If the pixel value exceeds the threshold, the image generation unit 24 determines "presence of contrast medium" and continues to measure the duration while keeping the flag at 1. The image generation unit 24 executes the processing from step S43 to step S45 for the pixel at the (i+1)th phase. If the pixel value of the pixel at the (i+1)th phase is smaller than the threshold, the image generation unit 24 stores the value of the duration timer as the stagnant time of the contrast medium at the pixel in the time interval from the time when the flag is set at 1 upon determination of "presence of contrast medium" to the current time in step S43, and holds the hue assigned to the pixel in the previous phase (step S44). With this operation, the image generation unit 24 generates a stagnant time image associated with the (i+1)th phase, with the contrast medium stagnant time at each position in the analysis area being represented by a hue, and the signal intensity from the contrast medium at each position in the analysis area being represented by a luminance (step S45). The monitor 14 then displays the generated stagnant time image associated with the (i+1)th phase, thereby updating the stagnant time image associated with the ith phase.

The control processor 25 executes analysis on the stagnant time in each of the subsequent phases. When a stagnant time image at the nth phase which is the last phase in the analysis period is generated, the control processor 25 terminates the stagnant time image generation (step S46).

With the above processing, in the case shown in FIG. 5, hue 1 is assigned to the pixel a in each phase after time t1. Hue 1 is assigned to the pixel b in each phase after time t2 to time t2+T. Hue 2 is assigned to the pixel b in each phase from time t2+T to time t4. Therefore, by observing the stagnant time image updated/displayed in chronological order in the form shown in FIG. 6, the observer can visually grasp that the duration of the contrast medium is short and the blood flow is relatively fast at the position corresponding to the pixel a, and that the duration is long and the blood flow is relatively slow at the position corresponding to the pixel b.

Figure 7:
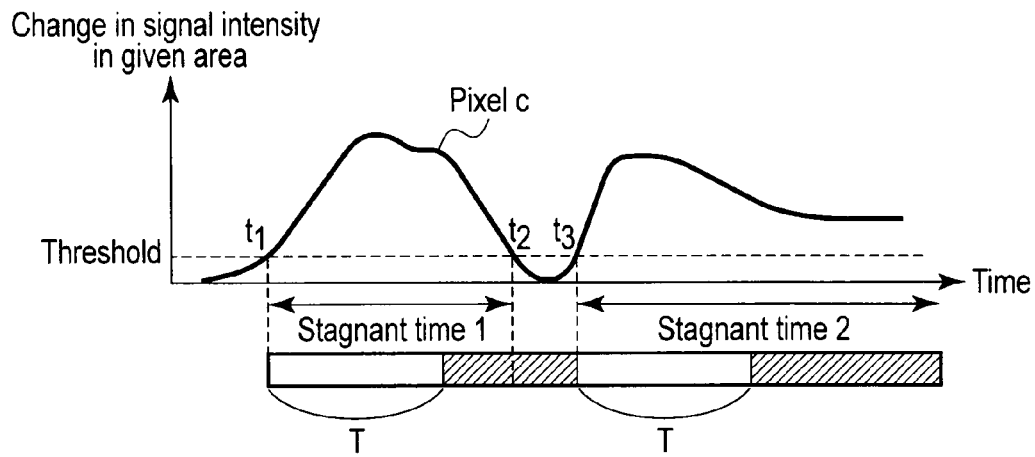
FIG. 7 is a graph for explaining duration/hue conversion processing for a pixel c in an analysis period.

If, for example, the TIC of a predetermined pixel c in an analysis area is represented by a curve like that shown in FIG. 7, hue 1 is assigned to the pixel c in each phase from time t1 to time t1+T, and hue 2 is assigned to the pixel in each phase from time t1+T to time t3. In addition, the stagnant time from time t1 to time t2 is stored at time t2, and the timer is reset. From time t3, measurement of a stagnant time is started again, and hue 1 is assigned in each phase from time t3 to time t3+T, and hue 2 is assigned in each phase after time t3+T. Therefore, by observing the analysis area which changes in hue from hue 1→hue 2→hue 1→hue 2 in the stagnant time image updated/displayed in chronological order in the form shown in FIG. 6, the observer can visually grasp how the stagnant time of the contrast medium changes from moment to moment at the position corresponding to the pixel c (that is, how the contrast medium becomes stagnant and inflows/outflows).

The image generation unit 24 then calculates the statistical value of the duration of each pixel (e.g., the maximum value, average value, minimum value, median value, or the like of the durations at each pixel in an analysis period) by using all the durations stored for the respective pixels. The image generation unit 24 generates a stagnant time image associated with the analysis period by determining a hue for each pixel in the analysis area based on the calculated statistical values and the hue correspondence map (step S47). The monitor 14 then displays the generated stagnant time image associated with the analysis period in a predetermined form.

Note that it is also possible to generate a stagnant time image associated with this analysis period by performing Max-Value Holding for each pixel in the analysis area throughout the analysis period.

[Quantitative Analysis of Stagnant Time/Display of Analysis Result Step S5]

Figure 8:
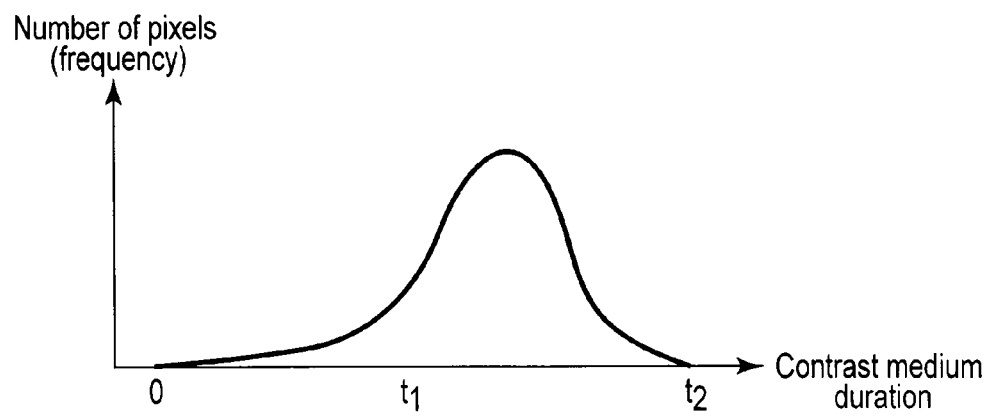
FIG. 8 is a graph showing an example of a duration distribution (histogram) associated with an area b shown in FIG. 6, which is generated in, for example, step S5.

The control processor 25 then executes quantitative analysis of the stagnant time by using the stagnant time image corresponding to each phase in the analysis period and displays the result (step S5). For example, the control processor 25 calculates the histogram of durations in the analysis area in a predetermined phase or the histogram of durations throughout a predetermined period of time in the analysis area. The control processor 25 also executes quantitative analysis to calculate a predetermined quantitative value such as the mode value (peak), center of gravity, or variance of the histogram, or the proportion of an area corresponding to a given duration or more to the region of interest. The monitor 14 displays the calculated histogram and the calculated quantitative value in, for example, the form shown in FIG. 8.

(First Modification)

The above embodiment has exemplified the case in which the TIC of each pixel in an analysis area is generated, and the processing of generating a stagnant time image which is shown in FIG. 4 is performed by using the TICs. However, this embodiment is not limited to this. It is possible to divide an analysis area into small areas each constituted by, for example, a plurality of pixels, generate TICs by using the average values or maximum values of pixel values in the respective small areas, and perform the processing of generating a stagnant time image by using the TICs.

(Second Modification)

Figure 9:
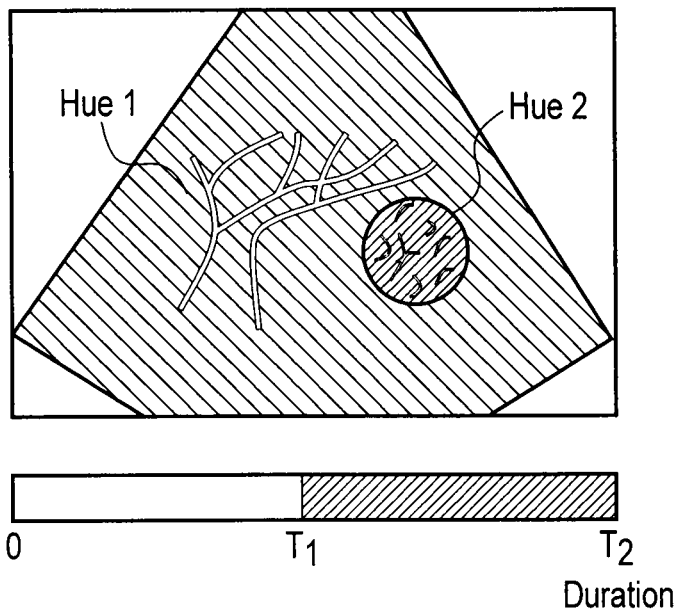
FIG. 9 is a view for explaining changing processing for a hue correspondence map.
Figure 10:
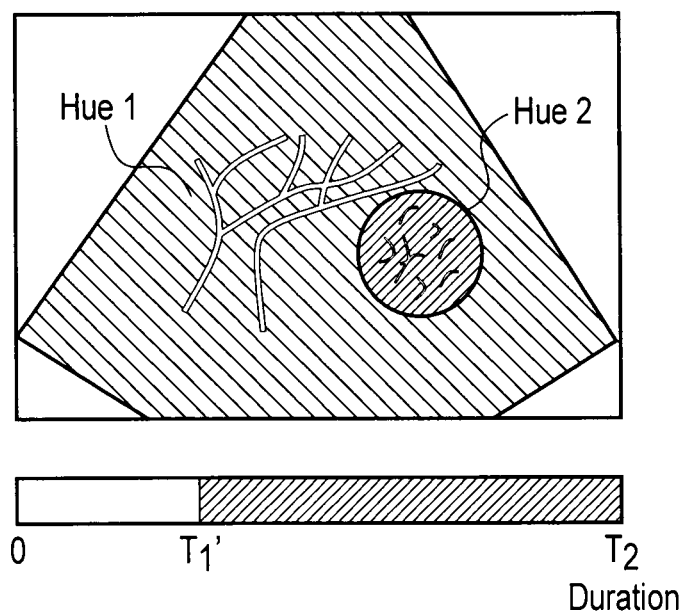
FIG. 10 is a view for explaining changing processing for a hue correspondence map.

A stagnant time as a hue boundary in a hue correspondence map can be arbitrarily changed and set. For example, in the hue correspondence map shown in FIG. 9, time T1 is defined as a boundary such that hue 1 changes to hue 2 at time T1. In this hue correspondence map, for example, time T1' shown in FIG. 10 may be re-defined by, for example, dragging the boundary line between hue 1 and hue 2 such that hue 1 changes to hue 2 at time T1'. Re-defining the hue correspondence map in this manner will update (enlarge) an area of the stagnant time image which corresponds to hue 2 from the area shown in FIG. 9 to the area shown in FIG. 10.

(Third Modification)

The number of hues defined by a hue correspondence map (i.e., the number of hues (different colors) representing stagnant times which are defined by a hue correspondence map) can be arbitrarily changed and set. In addition, stagnant times serving as the boundaries between the respective hues can be arbitrarily changed, as described in the second modification.

(Fourth Modification)

The operator may want to observe the behavior of each contrast medium bubble by using the ultrasonic probe 12 as a high-frequency probe. In this case, it is possible to use the analysis according to this embodiment in a state in which each contrast medium bubble is made to be easily observed by reducing the amount of contrast medium administered as compared with normal operation.

(Fifth Modification: Raw Data)

The above embodiment has exemplified the case in which the above contrast medium stagnant information generation processing is executed by using ultrasonic data constituted by pixels. However, this embodiment is not limited to this, and it is possible to execute the above contrast medium stagnant information generation processing by using raw data before it is input to the image generation unit 24.

(Effects)

This ultrasonic diagnostic apparatus measures a temporal change in each pixel value in an analysis area set in a scan area, and analyzes the stagnant time of a contrast medium for each pixel in the analysis area by using the measured temporal change in each pixel value. Based on the analysis result, this apparatus then generates a stagnant time image for the evaluation of the stagnant time of the contrast medium, and updates and displays the stagnant time image in chronological order. By observing the hues of a stagnant time image which is updated and displayed, the observer can visually grasp a position where the duration of a contrast medium is short and the blood flow is relatively fast, a position where the duration is long and the blood flow is relatively slow, and a position where the duration of the contrast medium changes from moment to moment and blood becomes stagnant and inflows/outflows. This improve the visual comprehension of the stagnant state of a contrast medium in the contrast echo method, and can be expected to contribute to tumor blood vessel evaluation and the determination of the effect of an antiangiogenic agent.

This ultrasonic diagnostic apparatus calculates the statistical value of the duration of each pixel (e.g., the maximum value, average value, minimum value, median value, or the like of the durations at each pixel in an analysis period) by using all the durations stored for the respective pixels. The ultrasonic diagnostic apparatus generates a stagnant time image associated with the analysis period by determining a hue for each pixel in the analysis area based on the calculated statistical values and the hue correspondence map. In addition, it is possible to execute quantitative analysis of stagnant times by using a stagnant time image corresponding to each phase in an analysis period and display the result. This improve the quantitative comprehension of the stagnant state of a contrast medium in the contrast echo method, and can be expected to contribute to tumor blood vessel evaluation and the determination of the effect of an antiangiogenic agent.

Second Embodiment

Figure 11:
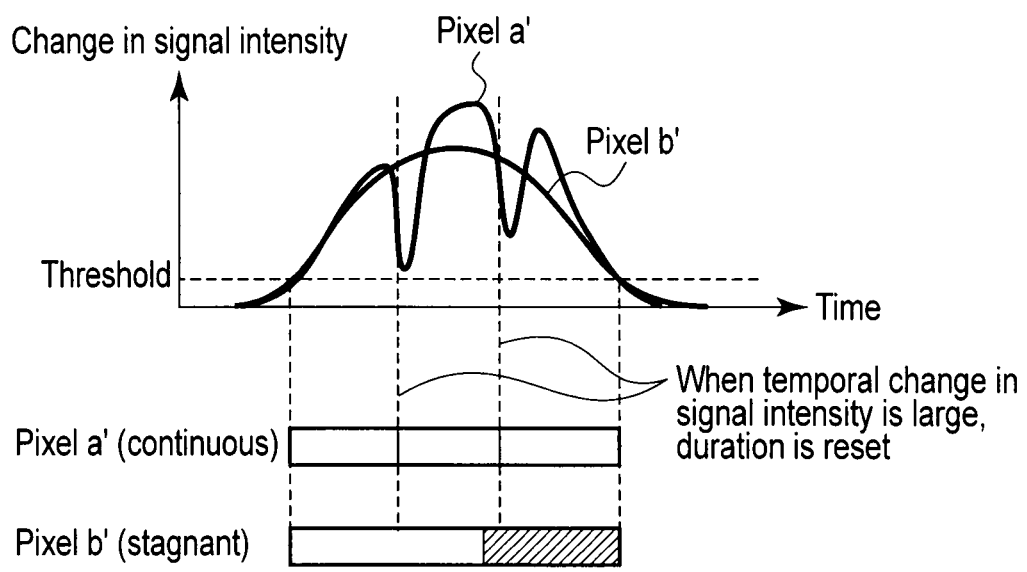
FIG. 11 is a graph showing TICs and hue correspondence maps associated with pixels a' and b'.

FIG. 11 shows TICs and hue correspondence maps for pixels a' and b'. As is obvious from each TIC in FIG. 11, the contrast medium continuously flows without becoming stagnant at the pixel a', and flows slow and becomes stagnant at the pixel b'. If the presence/absence of a contrast medium is determined in such a state of each area based on only comparison between signal intensities and a threshold as in the first embodiment, it is impossible to discriminate the pixel a' from the pixel b'. It may therefore be determined that the contrast medium flows slow and is stagnant at both the pixels a' and b'.

The second embodiment, therefore, focuses attention on a point that the flow rate of a contrast medium corresponds to temporal changes in signal intensity, and is configured to more accurately determine the presence/absence of a contrast medium at each position in consideration of temporal changes in signal intensity as well as the comparison between signal intensities and a threshold.

FIG. 12 is a flowchart showing a procedure for the processing of generating a stagnant time image according to this embodiment. This flowchart differs from that shown in FIG. 4 in the processing in steps S42a to S44. The contents of the processing in steps S42a to S44 will be described below.

An image generation unit 24 compares the pixel value (signal intensity) of each pixel with a preset threshold to determine whether the pixel value exceeds the threshold (that is, whether a contrast medium exists at a position corresponding to the pixel) (step S42a). If the pixel value exceeds the threshold, the image generation unit 24 calculates the difference between the signal intensities at the positions in consecutive frames and determines whether the absolute value of the difference is larger than a preset threshold (that is, whether the temporal change in signal intensity is larger than a reference value) (step S42b).

If the difference value is smaller than the threshold, the image generation unit 24 starts measuring the duration upon setting a flag representing the presence/absence of a contrast medium to 1 (corresponding to "presence of contrast medium") (or while keeping the flag at 1), and continues to measure the duration with the timer (step S43). If the pixel value is smaller than the threshold or the difference value is larger than the threshold, the image generation unit 24 stores the time from the instant the flag is set to 1 upon determining "presence of contrast medium" to the current time as the stagnant time of the contrast medium at the pixel, which is the value of the duration timer in step S43, and holds a hue assigned to the pixel in the previous phase (step S44).

This makes it possible to discriminate the blood flow at the pixel a' in FIG. 11 from the blood flow at the pixel b' and to accurately display the pixel a' with hue 1, at which the blood flow in a normal blood vessel or the like is relatively fast, and the pixel b' with hue 2, at which the contrast medium is stagnant in a tumor blood vessel or the like. Although the absolute value of the difference between signal intensities is used in this case, it is possible to reset the duration when the difference is larger or smaller than a preset threshold. In addition, it is possible to use the difference between frames at arbitrary intervals instead of the difference between consecutive frames.

Note that the present invention is not limited to each embodiment described above, and constituent elements can be modified and embodied in the execution stage within the spirit and scope of the invention. The following are concrete modifications.

(1) Each function associated with each embodiment can also be implemented by installing programs for executing the corresponding processing in a computer such as a workstation and expanding them in a memory. In this case, the programs which can cause the computer to execute the corresponding techniques can be distributed by being stored in recording media such as magnetic disks ((Floppy®) disks, hard disks, and the like), optical disks (CD-ROMs, DVDs, and the like), and semiconductor memories.

(2) In each embodiment, ultrasonic scanning on a two-dimensional area or three-dimensional area throughout an analysis period is the processing based on the premise that a slice position or volume position remains the same between phases. In practice, however, no matter how firmly the operator holds the probe, the hand may move or the probe may be moved by the respiration of a patient. That is, it is difficult to perfectly fix a slice or volume position. To correct the positional shift between consecutive slices or volumes by using, for example, the movement correction technique disclosed in Jpn. Pat. Appln. KOKAI Publication No. 2007-330764 is very useful when this proposed technique is used for actual examination.

(3) It is possible to measure and display the arrival time of a contrast medium (the time when the contrast medium has arrived first after the administration of the contrast medium), peak time, Wash-In time, Wash-Out time, and the like concurrently with the contrast medium stagnant information generation processing disclosed in each embodiment. It is possible to acquire these pieces of information by analyzing the TIC of each pixel in an analysis area. In such a case, a hue correspondence map can be defined as a map constituted by, for example, two axes, namely an arrival time axis and a duration axis. For example, in step S4, the image generation unit 24 executes hue assignment by using a hue correspondence map constituted by two axes, namely an arrival time axis and a duration axis.

(4) The second embodiment performs contrast medium stagnant information generation processing in consideration of temporal changes in signal intensity, in addition to comparison between signal intensities and a threshold. In contrast to this, it is possible to perform contrast medium stagnant information generation processing with reference to only temporal changes in signal intensity.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
an ultrasonic transmission/reception circuit configured to control repeated transmission of ultrasonic waves to a scan area, which is a two-dimensional or three-dimensional area of an object to which a contrast medium is administered, throughout an analysis period, control reception of reflected waves from the scan area, and acquire temporal sequence ultrasonic data corresponding to the scan area;

a control processor configured to
generate a luminance time curve associated with at least one analysis area included in the scan area by using the temporal sequence ultrasonic data in each phase in the analysis period,
determine a stagnant time of the contrast medium associated with said at least one analysis area using the generated luminance time curve,
generate a plurality of temporal sequence images based on the temporal sequence ultrasonic data,
analyze a brightness value of at least one analysis area in each of the plurality of temporal sequence images,
determine the stagnant time corresponding to a period when the brightness value of the at least one analysis area is exceeding a predetermined value,
assign a hue corresponding to the determined stagnant time for the at least one analysis area, and
generate a stagnant time image based on the hue; and
a display configured to display the stagnant time image.

2. The apparatus of claim 1, wherein the control processor generates the stagnant time image by using a correspondence map defining a correspondence relationship between durations of the contrast medium and hues.

3. The apparatus of claim 1, wherein the control processor generates the stagnant time image by using a second correspondence map defining a correspondence relationship between durations of the contrast medium, arrival times of the contrast medium, and hues.

4. The apparatus of claim 2, wherein the control processor is further configured to change the correspondence relationship of the correspondence map,
wherein when the control processor changes the correspondence relationship, the control processor generates the stagnant time image by using the correspondence map after the change.

5. The apparatus of claim 1, wherein the control processor compares a signal intensity in said at least one analysis area with a predetermined threshold in each phase in the analysis period by using the generated luminance time curve, and starts measuring the stagnant time at a timing when the signal intensity exceeds the predetermined threshold.

6. The apparatus of claim 1, wherein the control processor compares a signal intensity in said at least one analysis area with a predetermined threshold in each phase in the analysis period by using the generated luminance time curve, and finishes measuring the stagnant time at a timing when the signal intensity becomes lower than the predetermined threshold.

7. The apparatus of claim 1, wherein the control processor calculates a temporal change in signal intensity in said at least one analysis area using the generated luminance time curve, and starts measuring the stagnant time at a timing when the calculated temporal change becomes smaller than a predetermined threshold.

8. The apparatus of claim 1, wherein the control processor calculates a temporal change in signal intensity in said at least one analysis area using the generated luminance time curve, and finishes measuring the stagnant time at a timing when the calculated temporal change exceeds a predetermined threshold.

9. The apparatus of claim 1, wherein the control processor calculates a maximum value or average value of durations in the analysis period for said at least one analysis area, and
the control processor generates, for said at least one analysis area, the stagnant time image to which different hues are assigned in accordance with the maximum value or the average value.

10. The apparatus of claim 1, wherein the control processor calculates a predetermined quantitative value associated with the at least one analysis area by using the stagnant time image corresponding to each phase in the analysis period, and
the display displays the quantitative value in a predetermined form.

11. The apparatus of claim 1, wherein the control processor is further configured to correct a positional shift between phases in the scan area during acquisition of ultrasonic data acquired for each phase in the at least one analysis area.

12. The ultrasonic diagnosis apparatus of claim 1, wherein the control processor is configured to determine the stagnant time as a passage of time from the exceeding of the predetermined value to falling below the predetermined value.

13. A medical image diagnostic apparatus, comprising:
a control processor configured to
acquire temporal sequence ultrasonic data associated with a scan area, which is a two-dimensional or three-dimensional area of an object to which a contrast medium is administered, throughout an analysis period;
generate a luminance time curve associated with at least one analysis area included in the scan area by using the temporal sequence ultrasonic data in each phase in the analysis period,
determine a stagnant time of the contrast medium associated with said at least one analysis area using the generated luminance time curve,
generate a plurality of temporal sequence images based on the temporal sequence ultrasonic data,
analyze a brightness value of at least one analysis area in each of the plurality of temporal sequence images,
determine the stagnant time corresponding to a period when the brightness value of the at least one analysis area is exceeding a predetermined value,
assign a hue corresponding to the determined stagnant time for the at least one analysis area, and
generate a stagnant image based on the hue; and
a display configured to display the stagnant time image.

14. The apparatus of claim 13, wherein the control processor generates the stagnant time image by using a correspondence map defining a correspondence relationship between durations of the contrast medium and hues.

15. The apparatus of claim 13, wherein the control processor generates the stagnant time image by using a second correspondence map defining a correspondence relationship between durations of the contrast medium, arrival times of the contrast medium, and hues.

16. The apparatus of claim 14, wherein the control processor is further configured to change the correspondence relationship of the correspondence map,
wherein when the control processor changes the correspondence relationship, the control processor generates the stagnant time image by using the correspondence map after the change.

17. The apparatus of claim 13, wherein the control processor compares a signal intensity in said at least one analysis area with a predetermined threshold in each phase in the analysis period by using the generated luminance time curve, and starts measuring the stagnant time at a timing when the signal intensity exceeds the predetermined threshold.

18. The apparatus of claim 13, wherein the control processor compares a signal intensity in said at least one analysis area with a predetermined threshold in each phase in the analysis period by using the generated luminance time curve, and finishes measuring the stagnant time at a timing when the signal intensity becomes lower than the predetermined threshold.

19. The apparatus of claim 13, wherein the control processor calculates a temporal change in signal intensity in said at least one analysis area using the generated luminance time curve, and starts measuring the stagnant time at a timing when the calculated temporal change becomes smaller than a predetermined threshold.

20. The apparatus of claim 13, wherein the control processor calculates a temporal change in signal intensity in said at least one analysis area using the generated luminance time curve, and finishes measuring the stagnant time at a timing when the calculated temporal change exceeds a predetermined threshold.

21. The apparatus of claim 13, wherein the control processor calculates a maximum value or average value of durations in the analysis period for said at least one analysis area, and
the image generation unit generates, for said at least one analysis area, the stagnant time image to which different hues are assigned in accordance with the maximum value or the average value.

22. The apparatus of claim 13, wherein the control processor calculates a predetermined quantitative value associated with the at least one analysis area by using the stagnant time image corresponding to each phase in the analysis period, and
the display displays the quantitative value in a predetermined form.

23. The apparatus of claim 13, further comprising a correction unit configured to correct a positional shift between phases in the scan area during acquisition of ultrasonic data acquired for each phase in the at least one analysis area.

24. An ultrasonic image processing apparatus, comprising:
a memory configured to store temporal sequence ultrasonic data corresponding to a scan area, which is acquired by repeated transmission of ultrasonic waves to the scan area, which is a two-dimensional or three-dimensional area of an object to which a contrast medium is administered, throughout an analysis period, and reception of reflected waves from the scan area;
a control processor configured to
generate a luminance time curve associated with at least one analysis area included in the scan area by using the temporal sequence ultrasonic data in each phase in the analysis period,
determine a stagnant time of the contrast medium associated with said at least one analysis area using the generated luminance time curve,
generate a plurality of temporal sequence images based on the temporal sequence ultrasonic data,
analyze a brightness value of at least one analysis area in each of the plurality of temporal sequence images,
determine the stagnant time corresponding to a period when the brightness value of the at least one analysis area is exceeding a predetermined value,
assign a hue corresponding to the determined stagnant time for the at least one analysis area, and
generate a stagnant time image based on the hue; and
a display configured to display the stagnant time image.

* * * * *